(12) United States Patent
Garren et al.

(10) Patent No.: US 7,934,505 B2
(45) Date of Patent: May 3, 2011

(54) ENDOSCOPIC BITE BLOCK

(76) Inventors: Mary L. Garren, Carmel, CA (US);
Lloyd R. Garren, Carmel, CA (US);
Silas Lum, Monterey, CA (US)

(*) Notice: Subject to any disclaimer, the term of this patent is extended or adjusted under 35 U.S.C. 154(b) by 340 days.

(21) Appl. No.: 12/108,799

(22) Filed: Apr. 24, 2008

(65) Prior Publication Data

US 2009/0266368 A1   Oct. 29, 2009

(51) Int. Cl.
*A61C 5/14* (2006.01)
*A61M 16/00* (2006.01)
*A61M 25/00* (2006.01)
*A61B 1/04* (2006.01)

(52) U.S. Cl. .................. 128/859; 128/200.26; 600/120; 604/523

(58) Field of Classification Search ............ 128/200.26, 128/200.24, 207.17, 207.14, 206.29, 201.26, 128/206.22, 859, 861, 857, 846; 600/114, 600/237, 120, 153, 156; 604/523
See application file for complete search history.

(56) References Cited

U.S. PATENT DOCUMENTS

| | | | |
|---|---|---|---|
| 283,158 A | 8/1883 | Smith | |
| 329,908 A | 11/1885 | Johnson | |
| 348,932 A | 3/1886 | Rugg | |
| 4,270,529 A | 6/1981 | Muto | |
| 4,351,331 A | 9/1982 | Gereg | |
| 4,425,911 A | 1/1984 | Luomanen et al. | |
| 4,495,945 A | 1/1985 | Liegner | |
| 4,646,273 A | 2/1987 | Carlson et al. | |
| 5,009,227 A | 4/1991 | Nieuwstad | |
| 5,174,284 A | 12/1992 | Jackson | |
| 5,305,742 A | 4/1994 | Styers et al. | |
| 5,413,095 A | 5/1995 | Weaver | |
| 6,257,238 B1 | 7/2001 | Meah | |
| D536,441 S * | 2/2007 | Garren et al. | ................ D24/110 |
| 2007/0043264 A1* | 2/2007 | Gillis et al. | ................... 600/184 |
| 2007/0113844 A1* | 5/2007 | Garren et al. | ............ 128/200.26 |

OTHER PUBLICATIONS

Letter with enclosures from US Endoscopy to Lloyd Garren, MD Jul. 16, 2007.

\* cited by examiner

*Primary Examiner* — Patricia M Bianco
*Assistant Examiner* — Tarla R Patel
(74) *Attorney, Agent, or Firm* — Connolly Bove Lodge & Hutz LLP

(57) ABSTRACT

A bite block intended primarily for use with upper gastrointestinal endoscopy comprises a unitary body that fits into the mouth between the teeth or dental ridges. The bite block includes a central passageway large enough to accommodate a gastroscope. The bite block also has a surface which lies exterior to the oral cavity and extends around the outer surface of the lips. A suction wand is releasably connected to the body and extends into the intra-oral portion thereof where it forms an angle and allows suction drainage of pooled oral fluids from the cheek cavity. The interior tip of the suction wand has a terminal opening as well as multiple circumferentially arranged secondary openings adjacent the terminal opening all of which allow suction drainage of oral fluids with diminished occlusion by the oral tissues.

5 Claims, 4 Drawing Sheets

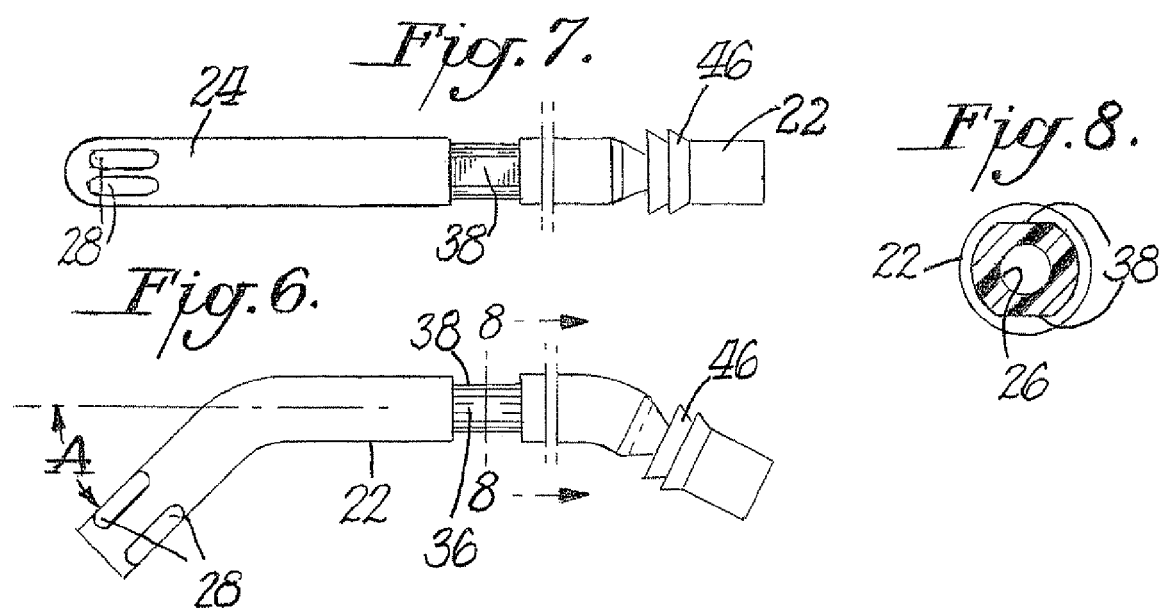

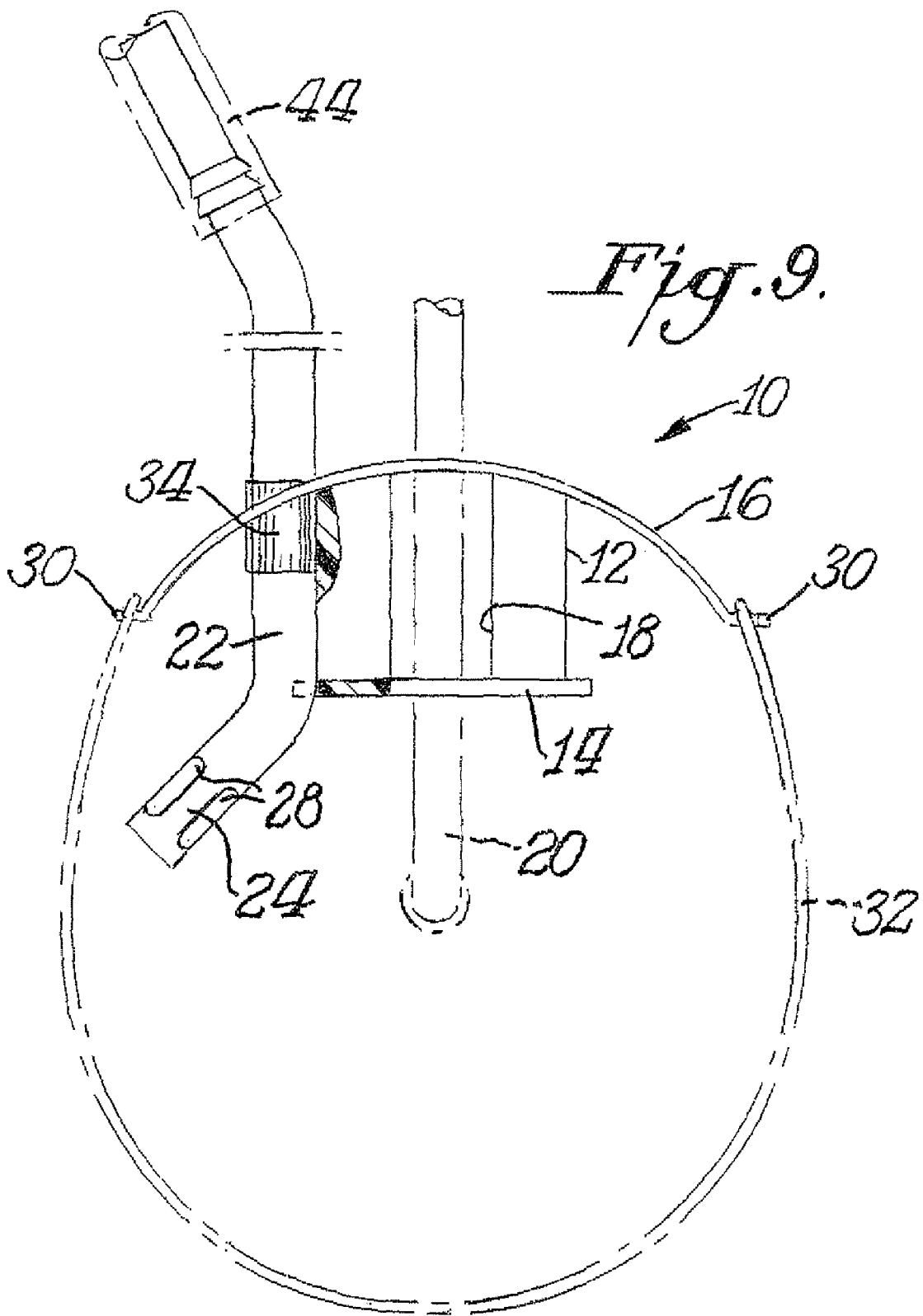

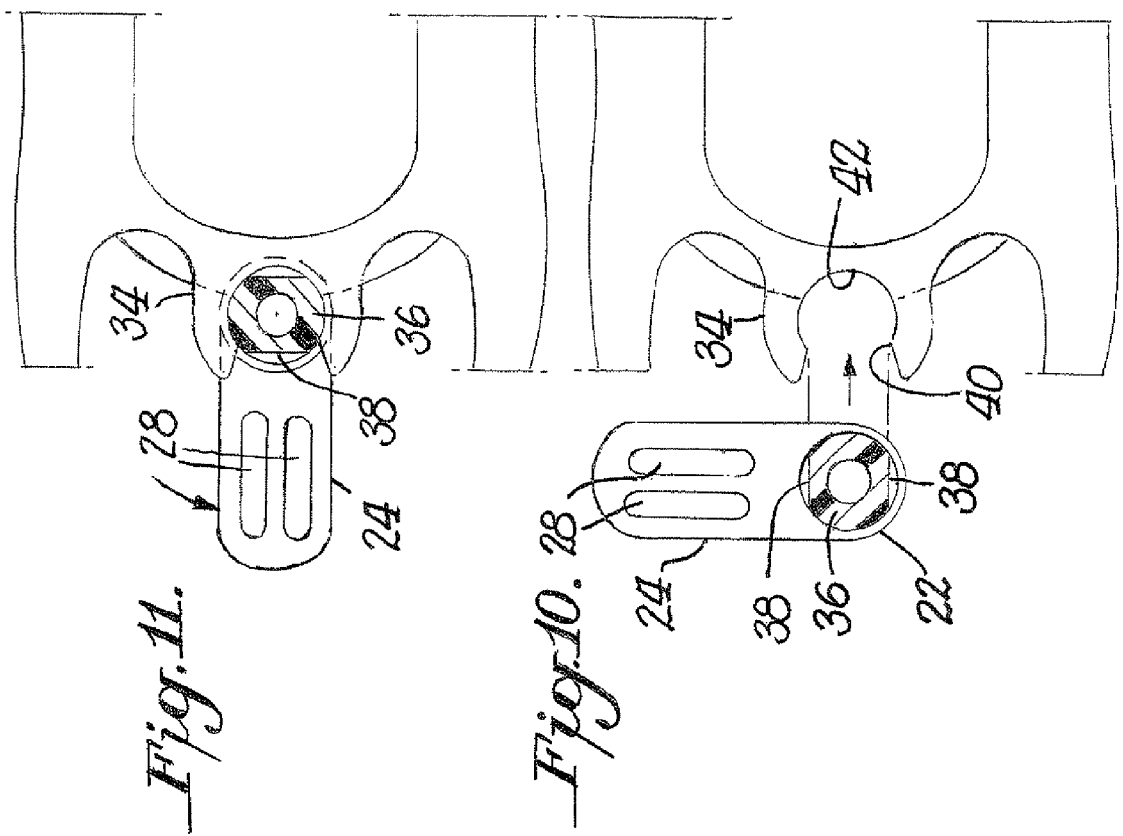

ENDOSCOPIC BITE BLOCK

BACKGROUND OF THE INVENTION

The present invention relates to an endoscopic bit block, and more particularly to a bite block that comprises a unitary body which allows for easy passage of an endoscope and which includes an integrated suction wand angled in a manner that catches and removes pooled oral fluids that accumulate during endoscopic procedures.

Instruments, such as endoscopes, are inserted through a person's mouth into the human body, in medical procedures. To prevent the patient from biting into the instrument, a bite block is used which is generally a plastic tube positioned in the patient's open mouth. The instrument is then inserted through the bite block opening into the stomach or other areas.

Presently, endoscopy is usually performed with the patient in the left lateral position using a bite block which maintains the teeth apart to protect the endoscope from damage by the teeth. This method makes it difficult to suction secretions and increases the risk of aspiration and potential procedure related complications. The currently available bite blocks require a second person and apparatus to accomplish oral suction. In addition, access for oral suction is difficult to obtain with currently available bite blocks. Bite blocks of one type or another are shown in U.S. Des. 283,158; U.S. Des 329,908; U.S. Des. 348,932; U.S. Pat. No. 4,270,529; U.S. Pat. No. 4,351,331; U.S. Pat. No. 4,425,911; U.S. Pat. No. 4,495,945; U.S. Pat. No. 4,646,273; U.S. Pat. No. 5,009,227; U.S. Pat. No. 5,174,284; U.S. Pat. No. 5,305,742; U.S. Pat. No. 5,413,095 and U.S. Pat. No. 6,257,238.

SUMMARY OF THE INVENTION

One of the objects of the present invention is to provide a bite block for endoscopy with a self-contained suction ability.

Another object of the present invention is an endoscopic bite block that enables mouth suction with decreased obstruction by oral tissues.

Still another object of the invention is an endoscopic bite block which is simple in construction, but highly effective and efficient in gastrointestinal endoscopy procedures.

Basically, the bite block of the present invention is extremely useful for performing endoscopy. The block provides protection for the endoscope while simultaneously allowing the evacuation of pooled intra-oral secretions without the labor of an additional person.

Fundamentally, the bite block of the present invention comprises a unitary body fabricated from plastic that is rigid enough to withstand pressure from apposition of the mandible to maxilla and having an exterior peri-labial component which is flexible enough to slightly mold to the exterior of the lips. The labial component has strap retainers at the sides thereof to allow attachment of an elastic strap for securing for bite block (via an elastic strap around the head connecting one side to the other).

In addition, the bite block has a suction wand extending from the exterior labial surface to the intra-oral surface. The suction wand at the labial surface has the ability to be connected to a commercial suction source by flexible tubing and the like. The terminal intra-oral portion of the suction wand has an angle which allows suctioning where secretions pool during endoscopy which is usually conducted with the patient in the left lateral position. In addition, the terminal portion of the intra-oral suction wand has several circumferentially located openings adjacent the terminal opening inwardly spaced from the terminal opening. This design aids in the prevention of complete occlusion of the suction wand by oral tissues.

In accordance with the present invention, an endoscopic bite block for a person undergoing upper gastrointestinal endoscopy comprises a unitary body having an intra-oral portion and an exterior portion. A central passageway extends through the unitary body, and the passageway is constructed and arranged to receive an endoscope. A suction wand is releasably attached to the unitary body, and the wand extends from the exterior to the intra-oral portions thereof. The suction wand includes an angled intra-oral end generally pointing to the check cavity of the person undergoing gastrointestinal endoscopy for suction removal of pooled oral fluids.

Preferably, the angled intra-oral end of the suction wand includes a terminal opening and several circumferentially located openings adjacent the terminal opening that allow suction drainage of pooled oral fluids with diminished occlusion by the oral tissues of the person undergoing gastrointestinal endoscopy. Moreover, the wand is releasably attached to the unitary body, and the angled intra-oral end of the suction wand is generally at an angle of about 45° to the main portion of the wand.

The exterior portion of the unitary body is per-labial and slightly flexible so as to mold to the exterior of the lips of the person undergoing gastrointestinal endoscopy. Moreover, the bite block may include an elastic strap, the ends of which are connected to the exterior portion of the unitary body for securement around the head of the person undergoing gastrointestinal endoscopy.

In accordance with the present invention, the unitary body of the endoscopic bite block includes an integral fitting on the exterior of the unitary body, and that fitting or wand holder is constructed and arranged to releasable receive the suction wand. In this regard, the wand includes a reduced diameter portion with opposite flat surfaces at a location along its length where it is attached to the wand holder of the unitary body. The wand holder has a passageway with a diameter generally equal to the reduced diameter portion of the wand, and an opening to the passageway is constructed and arranged to receive the opposite flat surfaces of the wand. Once the wand is so positioned in the passageway of the wand holder, the wand is rotated approximately 90° to thereby locate and hold the wand at its operating position.

BRIEF DESCRIPTION OF THE DRAWING

Novel features and advantages of the present invention in addition to those mentioned above will become apparent to persons of ordinary skill in the art from a reading of the following detailed description in conjunction with the accompanying drawings wherein similar reference characters refer to similar parts and in which:

FIG. 6 is a plan view of the suction wand shown in FIG. 1;

FIG. 7 is a side elevational view of the suction wand;

FIG. 8 is an enlarged sectional view taken along line 8-8 of FIG. 6;

FIG. 9 is a top plan view showing an elastic strap for holding the block in the mouth of the user and also showing details of the suction wand of the block; and FIGS. 10 and 11 are partial front views with portions broken away illustrating releasable attachment of the suction wand to the wand holder of the body of the bite block.

DETAILED DESCRIPTION OF THE INVENTION

Figure 5:
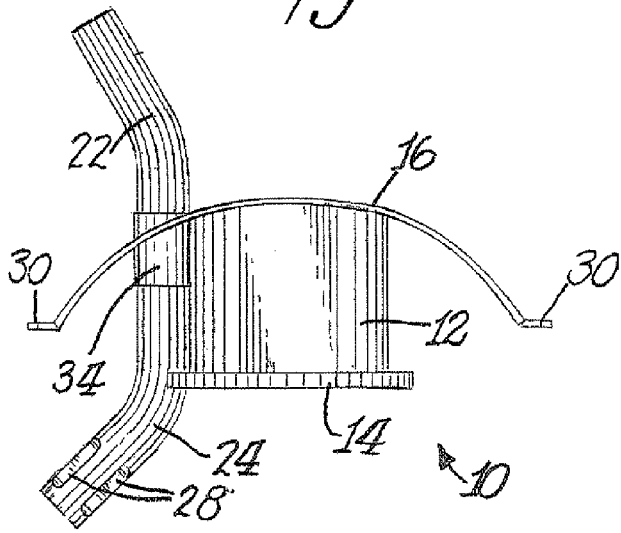
FIG. 5 is a top plan view of the endoscopic bite block shown in FIG. 1.
Figure 1:
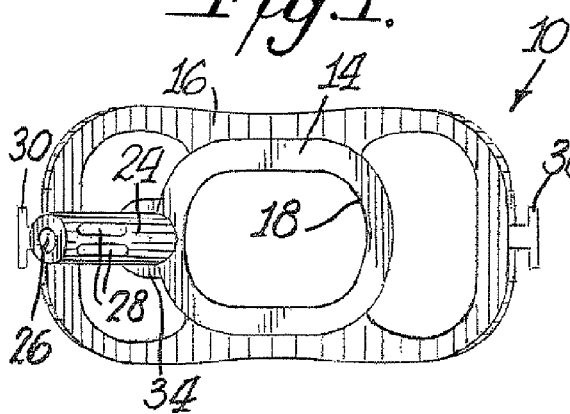
FIG. 1 is a rear elevational view of an endoscopic bite block, according to the present invention.
Figure 2:
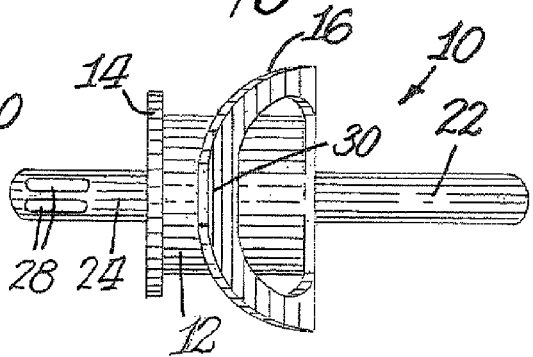
FIG. 2 is a right side elevational view of the endoscopic bite block shown in FIG. 1.
Figure 3:
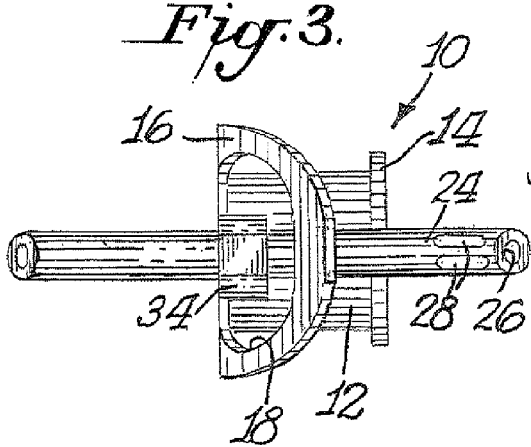
FIG. 3 is a left side elevational view of the endoscopic bite block shown in FIG. 1.
Figure 4:
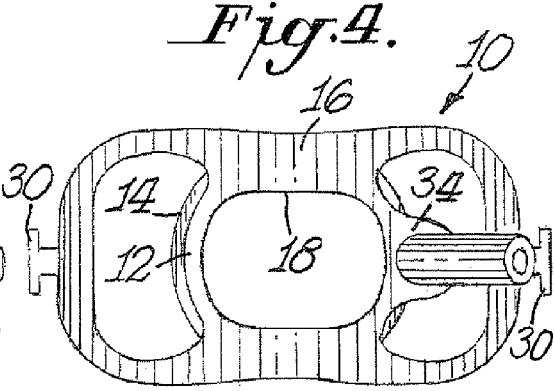
FIG. 4 is a front elevational view of the endoscopic bite block shown in FIG. 1.

Referring in more particularity to the drawings, FIGS. 1-5 illustrate an endoscopic bite block 10 for a person undergoing upper gastrointestinal endoscopy. The bite block comprises a unitary body 12 having an intra-oral portion 14 and an exterior portion 16. The unitary body may be formed from thermoplastic material by molding techniques known in the art. A central passageway 18 extends through the unitary body 12, and the passageway is arranged to receive an endoscope 20, such as shown in FIG. 9.

A suction wand 22 is releasably attached to the unitary body 12, and the wand extends from the exterior portion 16 to the intra-oral portion 14 of the unitary body 12. The suction wand 22 includes an angled intra-oral end 24 generally pointing to the left check cavity of a person undergoing gastrointestinal endoscopy for the suction removal of pooled oral fluids.

The angled intra-oral end 24 of the suction wand 22 includes a terminal opening 26 and several circumferentially located openings 28 that allow suction drainage of pooled oral fluids with diminished occlusion thereof by the oral tissues of the person undergoing gastrointestinal endoscopy. The openings 28 are adjacent the terminal opening 26, but spaced inwardly therefrom.

The central passageway 18 through the unitary body 12 of the bite block 10 and the suction wand 22 where the wand and body are releasably attached are oriented generally parallel to one another, and the intra-oral end 24 of the suction wand is generally angled to such orientation. Fundamentally, the angled intra-oral end 24 of the suction wand is formed at an angle A (FIG. 6) of about 45°, and as such the angled end 24 points to the left check cavity of the person undergoing gastrointestinal endoscopy. Normally the person lies on the left side during these procedures whereby the suction wand is properly positioned for suction drainage of pooled oral fluids in the left cheek cavity. However, should the person lie on the right side the block is easily inverted which then points the intra-oral end 24 of the suction wand 22 to the right.

The exterior portion 16 of the unitary body 12 is peri-labial and slightly flexible so as to mold to the exterior of the lips of the person undergoing gastrointestinal endoscopy. Strap retainers 30 are positioned on the right and left sides of the exterior portion 16 of the unitary body 12, and an elastic strap 32 is connected to the retainers 30 for securement around the head of the person undergoing gastrointestinal endoscopy. This particular feature of the invention is specifically shown in FIG. 9.

As shown in FIGS. 9-10, for example, the unitary body includes a wand holder 34 on the left side thereof for releasably connecting the suction wand 22 to the body of the bite block. At the location along the suction wand 22 where connection to the wand holder takes place, the suction wand has a reduced diameter portion 36 with opposite flat surfaces 38 that line up with an adjacent opening 40 in the wand holder. The holder 34 includes a passageway 42 having a diameter generally equal to the reduced diameter portion 36 of the wand. The wand is moved laterally toward the unitary body 12 into the opening 40 of the wand holder 34, as shown in FIG. 10. Such movement is easily performed since the distance between the flat surfaces 38 on the suction wand match the size of the opening 40 in the wand holder.

During such initial connection of the wand to its holder on the unitary body, the angled intra-oral end 24 is pointing either upwardly or downwardly relative to the unitary body. In FIG. 10 the intra-oral end 24 is pointing in a downward direction. However, once the suction wand is so positioned, the wand is rotated 90° to its operating position shown in FIGS. 5 and 11. Rotating the wand to its final position produces an increase in friction since the reduced diameter portion 36 of the wand at its point of attachment to the wand holder is matched with that of the diameter of the passageway 42 of the wand holder. This creates a semi-locked position of the suction wand 22 relative to the unitary body 12 so that the wand remains in place in its operating position during the endoscopic procedure.

The suction wand 22 is also designed for the suction or oral cavity fluids both on and off the unitary body 12 so the wand may be used in an independent manner, if desired.

In use, the suction wand 22 is connected by tubing 44 (FIG. 9) to a suitable suction source (not shown). FIGS. 6 and 7 illustrate one form of end configuration 46 for connection to such suction tubing 41. Also, the exterior portion 16 of the wand may be outwardly angled when the wand is in its use position, as sown in FIG. 6, for example. Moreover, since connection of the wand to the wand holder only takes place at the reduced diameter portion of the wand, positioning of the wand on the holder is always the same.

What is claimed is:

1. An endoscopic bite block for a person undergoing upper gastrointestinal endoscopy, the bite block comprising a unitary body having an intra-oral portion and an exterior portion, a central passageway extending through the unitary body constructed and arranged to receive an endoscope, a suction wand releasably connected to the unitary body and extending from the exterior to the intra-oral portions thereof, and the suction wand including an angled intra-oral end adapted to generally point to an oral cavity of a person undergoing gastrointestinal endoscopy for the suction removal of pooled oral fluids, and wherein the suction wand includes opposite flat surfaces at a point of connection to a wand holder, and the wand holder has an opening sized to receive the suction wand at the flat surfaces thereof, and wherein a friction fit is created when the wand is rotated approximately 90° to its operational position, and wherein the friction fit is created by the wand having a diameter at its point of connection to the wand holder matched to a passageway on the wand holder that receives the wand.

2. An endoscopic bite bock as in claim 1 wherein the angled intra-oral end of the suction wand includes a terminal opening and at least one circumferentially located secondary opening adjacent the terminal opening for suction drainage of pooled oral fluids.

3. An endoscopic bite block as in claim 1 wherein the central passageway and the suction wand are oriented generally parallel to one another at the point of attachment of the wand to the unitary body, and the angled intra-oral end of suction wand is generally 45° to such orientation.

4. An endoscopic bite block as in claim 1 wherein the exterior portion of the unitary body is peri-labial and slightly flexible so as to mold to the exterior of the lips of a person undergoing gastrointestinal endoscopy.

5. An endoscopic bite bock as in claim 1 including an elastic strap the ends of which are connected to the exterior portion of the unitary body for securement around the head of a person undergoing gastrointestinal endoscopy.

* * * * *